(12) United States Patent
Hotelling et al.

(10) Patent No.: US 8,400,408 B2
(45) Date of Patent: Mar. 19, 2013

(54) TOUCH SCREENS WITH TRANSPARENT CONDUCTIVE MATERIAL RESISTORS

(75) Inventors: Steve Porter Hotelling, San Jose, CA (US); Brian Richards Land, Redwood City, CA (US)

(73) Assignee: Apple Inc., Cupertino, CA (US)

(*) Notice: Subject to any disclaimer, the term of this patent is extended or adjusted under 35 U.S.C. 154(b) by 1226 days.

(21) Appl. No.: 11/818,311

(22) Filed: Jun. 13, 2007

(65) Prior Publication Data

US 2008/0309623 A1    Dec. 18, 2008

(51) Int. Cl.
*G06F 3/041* (2006.01)
(52) U.S. Cl. ........................................ 345/173
(58) Field of Classification Search .............. 345/173
See application file for complete search history.

(56) References Cited

U.S. PATENT DOCUMENTS

| | | |
|---|---|---|
| 4,205,418 A | 6/1980 | Przybylek |
| 4,786,767 A | 11/1988 | Kuhlman |
| 5,392,035 A | 2/1995 | Yoshikawa |
| 5,483,261 A | 1/1996 | Yasutake |
| 5,488,204 A | 1/1996 | Mead et al. |
| 5,825,352 A | 10/1998 | Bisset et al. |
| 5,835,079 A | 11/1998 | Shieh |
| 5,880,411 A | 3/1999 | Gillespie et al. |
| 5,945,973 A * | 8/1999 | Sakai et al. ............... 345/104 |
| 6,188,391 B1 | 2/2001 | Seely et al. |
| 6,310,610 B1 | 10/2001 | Beaton et al. |
| 6,323,846 B1 | 11/2001 | Westerman et al. |
| 6,690,387 B2 | 2/2004 | Zimmerman et al. |
| 6,970,160 B2 | 11/2005 | Mulligan et al. |
| 7,015,894 B2 | 3/2006 | Morohoshi |
| 7,184,064 B2 | 2/2007 | Zimmerman et al. |
| 7,349,136 B2 * | 3/2008 | Chui ............................ 359/237 |
| 2003/0222857 A1* | 12/2003 | Abileah ....................... 345/173 |
| 2004/0119701 A1* | 6/2004 | Mulligan et al. ............. 345/173 |
| 2006/0025081 A1* | 2/2006 | Zolfaghari ..................... 455/69 |
| 2006/0026521 A1 | 2/2006 | Hotelling et al. |
| 2006/0097991 A1* | 5/2006 | Hotelling et al. ............. 345/173 |
| 2006/0170658 A1* | 8/2006 | Nakamura et al. ............ 345/173 |
| 2006/0197753 A1 | 9/2006 | Hotelling |
| 2008/0143683 A1 | 6/2008 | Hotelling |
| 2008/0158183 A1 | 7/2008 | Hotelling et al. |

FOREIGN PATENT DOCUMENTS

| | | |
|---|---|---|
| EP | 1197835 A2 | 4/2002 |
| EP | 1576570 A2 | 9/2005 |
| JP | 02-101768 A | 4/1990 |
| JP | 03-059516 A | 3/1991 |
| JP | 08-137607 A | 5/1996 |
| JP | 2000-163031 A | 6/2000 |

(Continued)

OTHER PUBLICATIONS

International Search Report mailed Aug. 25, 2008, for PCT Application No. PCT/US2008/066762, three pages.

(Continued)

*Primary Examiner* — Seokyun Moon
(74) *Attorney, Agent, or Firm* — Morrison & Foerster LLP (57) ABSTRACT

Systems and methods for touch screens with integrated transparent conductive material resistors are provided. Metal traces on the surface of a touch screen may be subject to radio-frequency interference (RFI) that can adversely affect the performance of the touch screen. Transparent conductive material resistors inserted within the metal trace paths can be used to form low-pass filters which can reduce the affect of the RFI.

22 Claims, 11 Drawing Sheets

FOREIGN PATENT DOCUMENTS

| | | |
|---|---|---|
| JP | 2002-342033 A | 11/2002 |
| JP | 2006-511879 A | 4/2006 |
| WO | WO-2004/061808 A2 | 7/2004 |
| WO | WO-2004/061808 A3 | 7/2004 |
| WO | WO 2007/021571 A2 | 2/2007 |
| WO | WO-2008/157253 A1 | 12/2008 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements of the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

TOUCH SCREENS WITH TRANSPARENT CONDUCTIVE MATERIAL RESISTORS

BACKGROUND OF THE INVENTION

This relates to touch screen systems and methods having integrated transparent conductive material resistors. The transparent conductive material resistors can be make from indium tin oxide (ITO), conductive clear polymer, antimony tin oxide (ATO), or other suitable materials.

There exist many styles of input devices for performing operations in a computer system. The operations generally correspond to moving a cursor and/or making selections on a display screen. By way of example, the input devices may include buttons or keys, mice, trackballs, touch pads, joy sticks, touch screens and the like. Touch screens, in particular, are becoming increasingly popular because of their ease and versatility of operation as well as to their declining price. Touch screens allow a user to make selections and move a cursor by simply touching the display screen via a finger or stylus. In general, the touch screen recognizes the touch and position of the touch on the display screen and the computer system interprets the touch and thereafter performs an action based on the touch event.

Touch screens typically include a touch panel, a controller and a software driver. The touch panel is a clear panel with a touch sensitive surface. The touch panel is positioned in front of a display screen so that the touch sensitive surface covers the viewable area of the display screen. The touch panel registers touch events (the touching of fingers or other objects upon a touch sensitive surface) and sends these signals to the controller. The controller processes these signals and sends the data to the computer system. The software driver translates the touch events into computer events.

Touch panels can include an array of touch sensors capable of detecting touch events. Some touch panels can detect multiple touches (the touching of fingers or other objects upon a touch-sensitive surface at distinct locations at about the same time) and near touches (fingers or other objects within the near-field detection capabilities of their touch sensors), and identify and track their locations. Those touch panels capable of detecting multiple touches may be referred to as multi-touch panels.

Mutual capacitive touch panels can be formed from rows and columns of traces on opposite sides of a dielectric. At the "intersections" of the traces, where the traces pass above and below each other (but do not make direct electrical contact with each other), the traces essentially form two electrodes with a mutual capacitance therebetween. To scan a sensor panel, a stimulus can be applied to one row with all other rows held at DC voltage levels. When a row is stimulated, a modulated output signal can be capacitively coupled onto the columns of the sensor panel. The columns can be connected to analog channels (also referred to herein as event detection and demodulation circuits). When the panel is touched or nearly-touched, a small amount of charge is drawn to the point of contact. For every row that is stimulated, each analog channel connected to a column generates an output value representative of an amount of change in the modulated output signal due to a touch or hover event occurring at the sensor located at the intersection of the stimulated row and the connected column. After analog channel output values are obtained for every column in the sensor panel, a new row is stimulated (with all other rows once again held at DC voltage levels), and additional analog channel output values are obtained. When all rows have been stimulated and analog channel output values have been obtained, the sensor panel is said to have been "scanned," and a complete "image" of touch or hover can be obtained over the entire sensor panel. This image of touch or hover can include an analog channel output value for every pixel (row and column) in the panel, each output value representative of the amount of touch or hover that was detected at that particular location.

Metal traces that are etched into the touch panels can be used to transmit charges from the panel surface to the event detection and demodulation circuits connected to the panel. As the size of a touch screen increases, the length of the metal traces etched into the touch panel also increases. These longer metal traces can act as antennas and cause radio-frequency interference (RFI) signals to be brought into the touch panel circuits and controller. RFI is any undesirable RF signal that interferes with the integrity of electronics and electrical systems. These RFI signals may adversely affect the operation of the touch screen.

Accordingly, what is needed are systems and methods for reducing the affect of RFI signals in touch screens.

SUMMARY OF THE INVENTION

Systems and methods for touch screens with transparent conductive material resistors are provided.

Transparent conductive material resistors can be inserted into the metal traces that are etched into the touch panels which are used to transmit charges from the panel surface to the capacitance detection circuitry connected to the panel. For example, the metal traces can be broken and transparent conductive material resistors can be formed inside these breaks. The resistance of these transparent conductive material resistors in combination with the inherent capacitance values of the circuitry and connectors that are connected to the touch panel can form a low-pass filter that is capable of blocking the RFI signals.

Inserting the transparent conductive material resistors within the metal traces in this manner can be accomplished with little or no incremental cost because the transparent conductive material may already be patterned on the surface of the touch panel to create the electrode rows and columns used to form the touch sensors. These electrode rows and columns are generally formed by depositing a transparent conductive material layer over the substrate surface, and then by etching away portions of the transparent conductive material layer in order to form the traces. Therefore, the transparent conductive material resistors can be formed as part of the process of creating the transparent conductive material electrode rows and columns. Instead of etching away all of the extra portions of the transparent conductive material layer, some of the transparent conductive material portions may be kept to serve as transparent conductive material resistors.

BRIEF DESCRIPTION OF THE DRAWINGS

The above and other features of the present invention, its nature and various advantages will become more apparent upon consideration of the following detailed description, taken in conjunction with the accompanying drawings, in which like reference characters refer to like parts throughout, and in which.

DETAILED DESCRIPTION OF THE INVENTION

Commonly assigned Steve Hotelling et al. U.S. patent application Ser. No. 10/840,862, filed May 6, 2004, entitled "MULTIPOINT TOUCHSCREEN" is hereby incorporated by reference in its entirety.

Commonly assigned Steve Hotelling et al. U.S. patent application Ser. No. 11/650,182, filed Jan. 3, 2007, entitled "DOUBLE-SIDED TOUCH-SENSITIVE PANEL WITH SHIELD AND DRIVE COMBINED LAYER" is hereby incorporated by reference in its entirety.

Commonly assigned Steve Hotelling U.S. patent application Ser. No. 11/818,394, filed Jun. 13, 2007, entitled "PET-BASED TOUCHPAD" is hereby incorporated by reference in its entirety.

Figure 1:
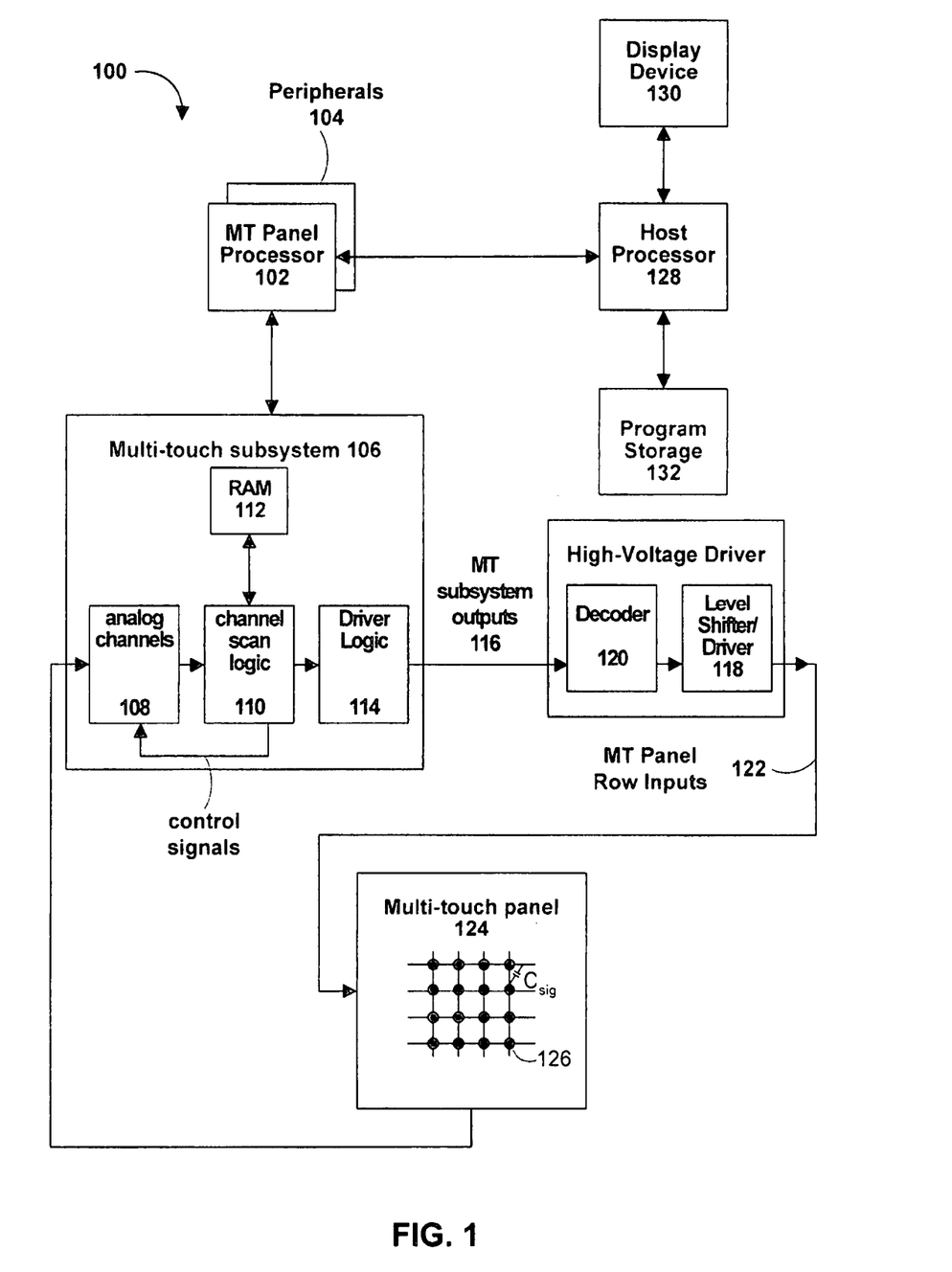
FIG. 1 shows an exemplary touch screen computing system operable with a capacitive touch panel in accordance with an embodiment of the present invention.

FIG. 1 shows an exemplary touch screen computing system 100 operable with capacitive touch panel 124 according to embodiments of this invention. Touch panel 124 can be connected to other components in computing system 100 through connectors integrally formed on the sensor panel, or using flex circuits. Computing system 100 can include one or more panel processors 102 and peripherals 104, and panel subsystem 106. The one or more processors 102 can include, for example, ARM968 processors or other processors with similar functionality and capabilities. However, in other embodiments, the panel processor functionality can be implemented instead by dedicated logic such as a state machine. Peripherals 104 can include, but are not limited to, random access memory (RAM) or other types of memory or storage, watchdog timers and the like.

Panel subsystem 106 can include, but is not limited to, one or more analog channels 108, channel scan logic 110 and driver logic 114. Channel scan logic 110 can access RAM 112, autonomously read data from the analog channels and provide control for the analog channels. This control can include multiplexing columns of multi-touch panel 124 to analog channels 108. In addition, channel scan logic 110 can control the driver logic and stimulation signals being selectively applied to rows of multi-touch panel 124. In some embodiments, panel subsystem 106, panel processor 102 and peripherals 104 can be integrated into a single application specific integrated circuit (ASIC).

Driver logic 114 can provide multiple panel subsystem outputs 116 and can present a proprietary interface that drives high voltage driver 118. High voltage driver 118 can provide level shifting from a low voltage level (e.g. complementary metal oxide semiconductor (CMOS) levels) to a higher voltage level, providing a better signal-to-noise (S/N) ratio for noise reduction purposes. The high voltage driver outputs can be sent to decoder 120, which can selectively connect one or more high voltage driver outputs to one or more panel row inputs 122 through a proprietary interface and enable the use of fewer high voltage driver circuits in the high voltage driver 118. Each panel row input 122 can drive one or more rows in a multi-touch panel 124. In some embodiments, high voltage driver 118 and decoder 120 can be integrated into a single ASIC. However, in other embodiments high voltage driver 118 and decoder 120 can be integrated into driver logic 114, and in still other embodiments high voltage driver 118 and decoder 120 can be eliminated entirely.

Computing system 100 can also include host processor 128 for receiving outputs from panel processor 102 and performing actions based on the outputs that can include, but are not limited to, moving an object such as a cursor or pointer, scrolling or panning, adjusting control settings, opening a file or document, viewing a menu, making a selection, executing instructions, operating a peripheral device connected to the host device, answering a telephone call, placing a telephone call, terminating a telephone call, changing the volume or audio settings, storing information related to telephone communications such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, and/or the like. Host processor 128 can also perform additional functions that may not be related to panel processing, and can be coupled to program storage 132 and display device 130 such as a liquid crystal display (LCD) for providing a UI to a user of the device.

As mentioned above, multi-touch panel 124 can in some embodiments include a capacitive sensing medium having a plurality of row traces or driving lines and a plurality of column traces or sensing lines separated by a dielectric. In some embodiments, the dielectric material can be transparent, such as polyethylene terephthalate (PET), glass, or another material such as Mylar. The row and column traces can be formed from a transparent conductive material such as indium tin oxide (ITO), conductive clear polymer, or antimony tin oxide (ATO), although other non-transparent materials such as copper can also be used. In some embodiments, the row and column traces can be perpendicular to each other, although in other embodiments other non-orthogonal orientations are possible. For example, in a polar coordinate system, the sensing lines can be concentric circles and the driving lines can be radially extending lines (or vice versa). It should be understood, therefore, that the terms "row" and "column," "first dimension" and "second dimension," or "first axis" and "second axis" as may be used herein are intended to encompass not only orthogonal grids, but the intersecting traces of other geometric configurations having first and second dimensions (e.g. the concentric and radial lines of a polar-coordinate arrangement).

At the "intersections" of the traces, where the traces pass above and below each other (but do not make direct electrical contact with each other), the traces essentially form two electrodes (although more than two traces can intersect as well). Each intersection of row and column traces can represent a capacitive sensing node and can be viewed as picture element (pixel) 126, which can be particularly useful when multi-touch panel 124 is viewed as capturing an "image" of touch. (In other words, after panel subsystem 106 has determined whether a touch event has been detected at each touch sensor in multi-touch panel 124, the pattern of touch sensors in the multi-touch panel at which a touch event occurred can be viewed as an "image" of touch (e.g. a pattern of fingers touching the panel).) When the two electrodes are at different potentials, each pixel can have an inherent self or mutual capacitance formed between the row and column electrodes of the pixel. If an AC signal is applied to one of the electrodes, such as by exciting the row electrode with an AC voltage at a particular frequency, an electric field and an AC or signal capacitance can be formed between the electrodes, referred to as Csig. The presence of a finger or other object near or on multi-touch panel 124 can be detected by measuring changes to Csig. The columns of multi-touch panel 124 can drive one or more analog channels 108 in panel subsystem 106. In some embodiments, each column is coupled to one dedicated analog channel 108. However, in other embodiments, the columns can be couplable via an analog switch to a fewer number of analog channels 108.

Figure 2:
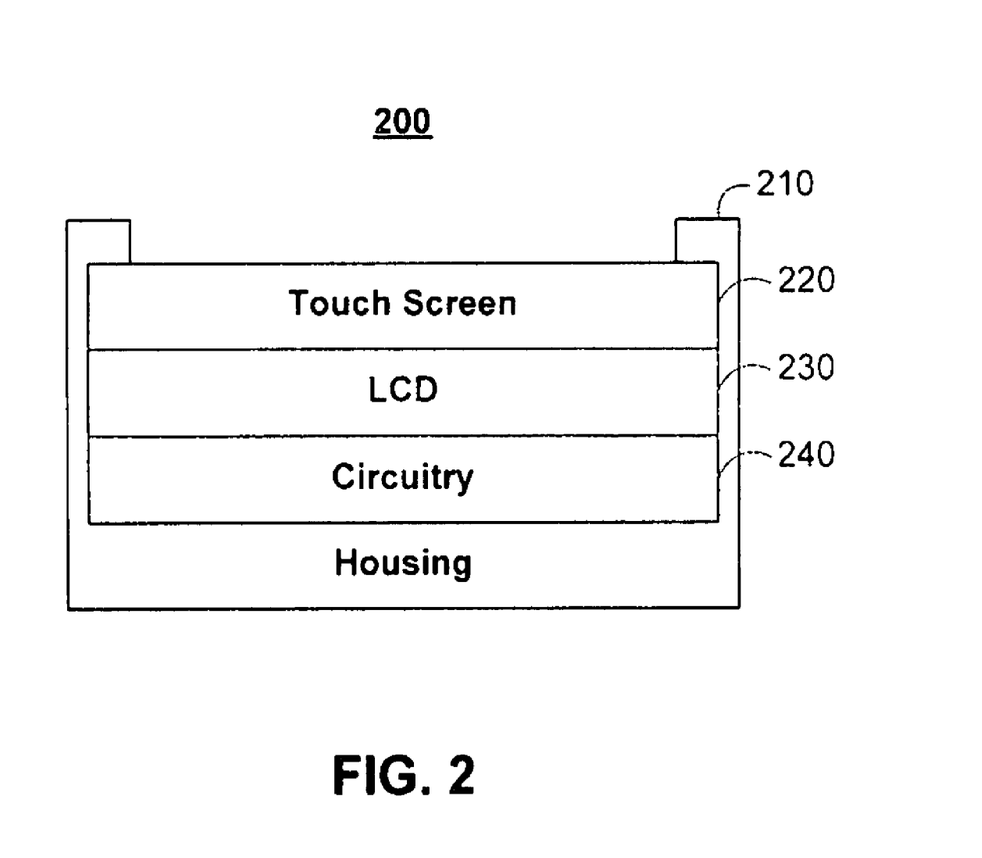
FIG. 2 shows an exploded perspective view of an illustrative touch screen computing system in accordance with an embodiment of the present invention.

FIG. 2 shows an exploded perspective view of an illustrative touch screen computing system 200. Touch screen system 200 includes liquid crystal display (LCD) 230 and transparent touch screen 220 positioned in front of LCD 230. LCD 230 can be configured to display a graphical user interface (GUI) including perhaps a pointer or cursor as well as other information to a user. Touch screen 220, on the other hand, is an input device that is sensitive to a user's touch, allowing a user to interact with the graphical user interface on LCD 230. By way of example, touch screen 220 may allow a user to move an input pointer or make selections on the graphical user interface by simply pointing at the GUI on LCD 230.

Housing 210 encloses and protects touch screen 220, LCD 230, as well as circuitry 240. Circuitry 240 can include controller circuitry for touch screen 220, and LCD 230 as well as additional circuitry including processor circuitry, memory circuitry, and power circuitry. Touch screen system 200 may be a stand alone unit or it may integrated with other devices. When stand alone, touch screen system 200 (or each of its components) can act like a peripheral device that includes its own housing and that can be coupled to a host device through wired or wireless connections. When integrated, touch screen system 200 shares housing 210 and is hard wired into the host device thereby forming a single unit. By way of example, touch screen system 200 may be disposed inside a variety of host devices including but not limited to general purpose computers such as a desktop, laptop or tablet computers, handhelds such as PDAs and media players such as music players, peripheral devices such as cameras, printers and/or the like, or hybrid computer/phone devices.

Figure 3:
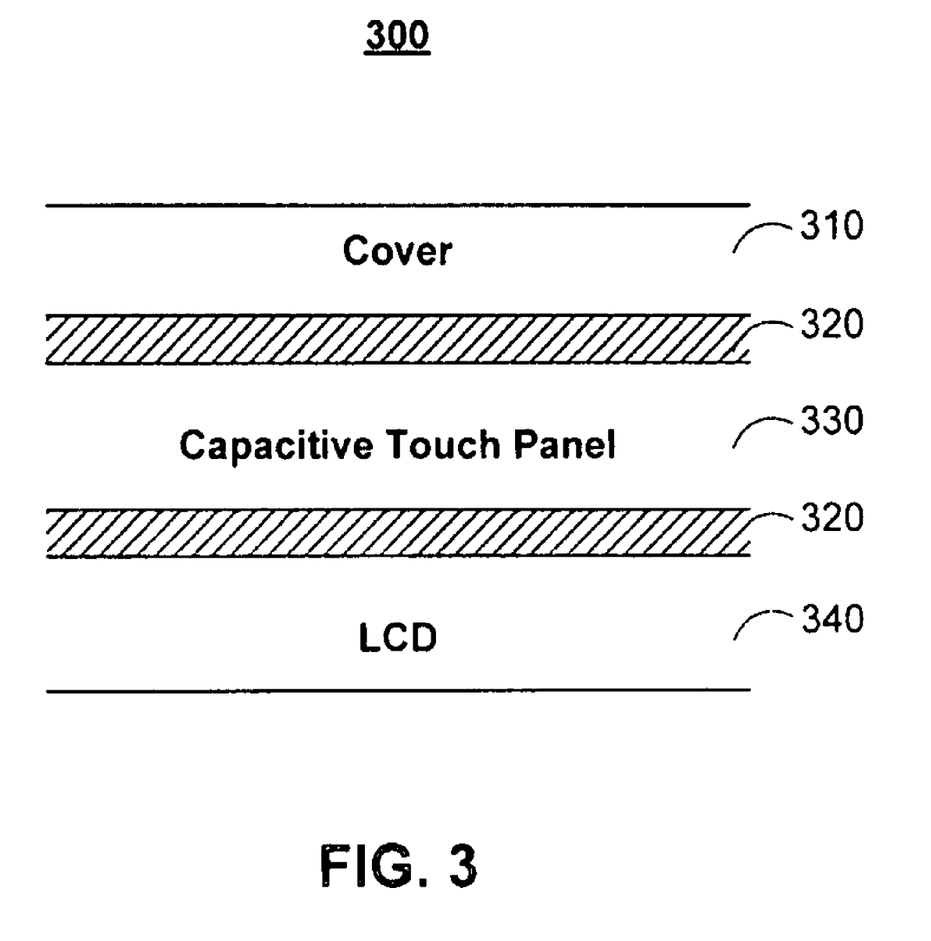
FIG. 3 shows a detailed cross-sectional view of an illustrative touch screen in accordance with an embodiment of the present invention.

FIG. 3 shows a detailed cross-sectional view of illustrative touch screen 300. Touch screen 300 includes capacitive touch panel 330 which is sandwiched between protective cover 310 and LCD 340. LCD 340 can correspond to any conventional LCD display known in the art. Although not shown, the LCD 340 typically includes various layers including a fluorescent panel, polarizing filters, a layer of liquid crystal cells, a color filter and the like.

Protective cover 310 serves to protect the under layers and provide a surface for allowing an object to slide thereon. Cover 310 can be suitably thin to allow for sufficient coupling to capacitive touch panel 330. Cover 310 can be formed from any suitable clear material such as glass and plastic. In addition, cover 310 can be treated with coatings to reduce stiction when touching and reduce glare when viewing the underlying LCD 310. By way of example, a low stiction/anti reflective coating can be applied over the cover sheet 310.

Touch screen 300 also includes various bonding layers 320. Bonding layers 320 bond capacitive touch panel to LCD 340 and cover 310 together to form the laminated structure and to provide rigidity and stiffness to the laminated structure. In essence, bonding layers 320 help to produce a monolithic sheet that is stronger than each of the individual layers taken alone. In some cases, the bonding agent includes an index matching material to improve the visual appearance of the touch screen 300. In some embodiments, one or both bonding layers 320 can be eliminated without affecting the performance of the touch screen.

Figure 4:
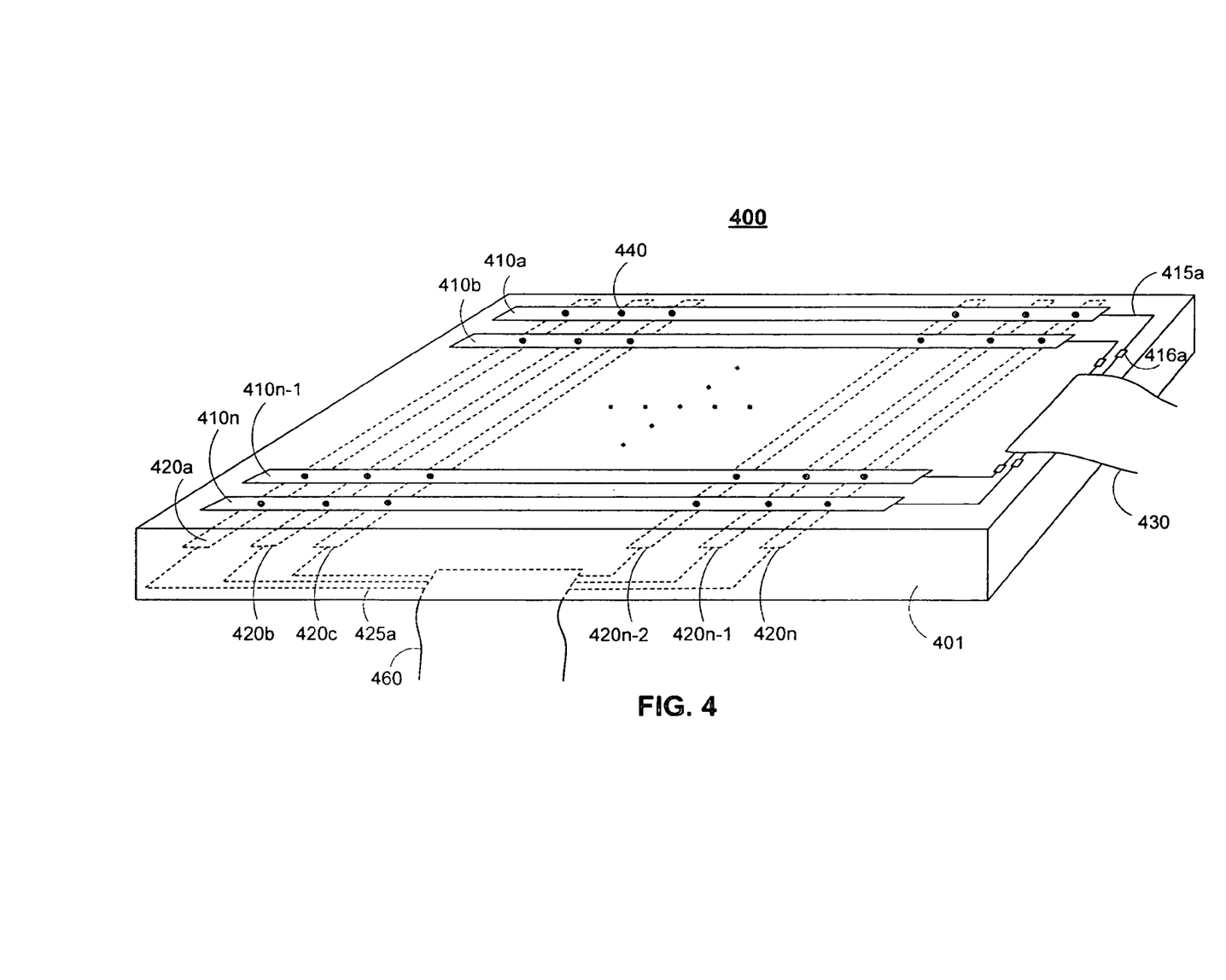
FIG. 4 shows an illustrative capacitive touch panel with integrated transparent conductive material resistors in accordance with an embodiment of the present invention.

FIG. 4 shows an illustrative capacitive touch panel 400 with integrated transparent conductive material resistors. Touch panel 400 includes a plurality of capacitance sensing nodes 440. The capacitive sensing nodes may be widely varied. For example, the capacitive sensing nodes may be based on self capacitance or mutual capacitance. In self capacitance, the "self" capacitance of a single electrode is measured as for example relative to ground. In mutual capacitance, the mutual capacitance between at least first and second electrodes is measured. In either case, each node 440 can work independent of the other nodes 440 so as to produce simultaneously occurring signals representative of different points on the touch panel 400.

As shown, the touch panel 400 includes a two layer grid of spatially separated non-overlapping lines. In the illustrated embodiment touch panel 400 includes transparent conductive material column traces 410 on the top surface and transparent conductive material row traces 420 on the bottom surface. In most cases, the lines on each surface are parallel one another. Furthermore, although in different planes, the lines on the different surfaces are configured to intersect or cross in order to produce capacitive sensing nodes 440, which each represent different coordinates in the plane of the touch panel 400. The nodes 440 are configured to receive capacitive input from an object touching the touch panel 400 in the vicinity of the node 440. When an object is proximate to a node 440, the object steals charge thereby affecting the capacitance at the node 440.

As previously described, row traces 420 are individually stimulated with an AC signal while column traces 410 are connected to capacitive sensing circuitry (not shown) that may continuously sense all of column traces 410. The capacitive sensing circuitry typically includes one or more sensor ICs that measure the capacitance in each of column traces 410 and reports its findings to a host controller. The sensor ICs may, for example, convert the analog capacitive signals to digital data and thereafter transmit the digital data over a serial bus to a host controller. Any number of sensor ICs may be used. For example, a sensor IC may be used for all column traces 410, or multiple sensor ICs may be used for a single or group of column traces 410. In most cases, the sensor ICs report tracking signals, which are a function of both the position of the node 440 and the intensity of the capacitance at the node 440.

Column traces 410 and row traces 420 can be placed on the surfaces of dielectric member 401 using any suitable patterning technique including for example, deposition, etching, printing and the like. Because row traces 420 may be either stimulated with an AC signal or held at a DC voltage level, and because column traces 410 need to be connected to analog channels so that modulated output signals can be detected, demodulated and converted to output values, electrical connections must be formed with row traces 420 and column traces 410.

Flex circuits can be electrically connected directly to row traces 420 and column traces 410. However, as the size of touch panel 400 increases, the size of the flex circuits required to couple directly to row traces 420 and column traces 410 also increases. In order to reduce the size of the flex circuits and to allow for greater variation in the placement of flex circuits, metal traces 415 and 425 can be used to connect row traces 420 and column traces 410 to the flex circuits.

Figure 5:
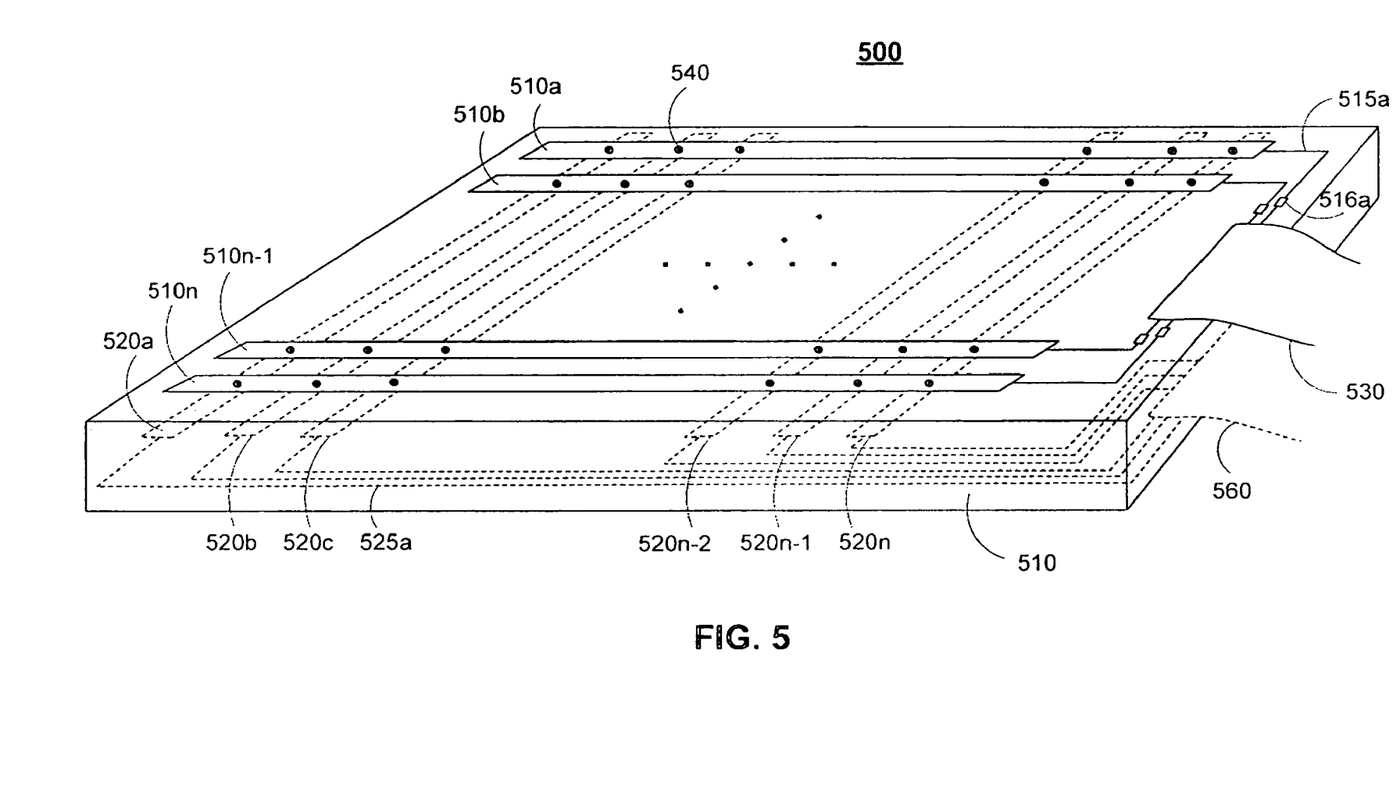
FIG. 5 shows an illustrative touch panel with integrated transparent conductive material resistors in which the flex circuits are bonded to the same edge, on directly opposite sides of the panel in accordance with an embodiment of the present invention.
Figure 6:
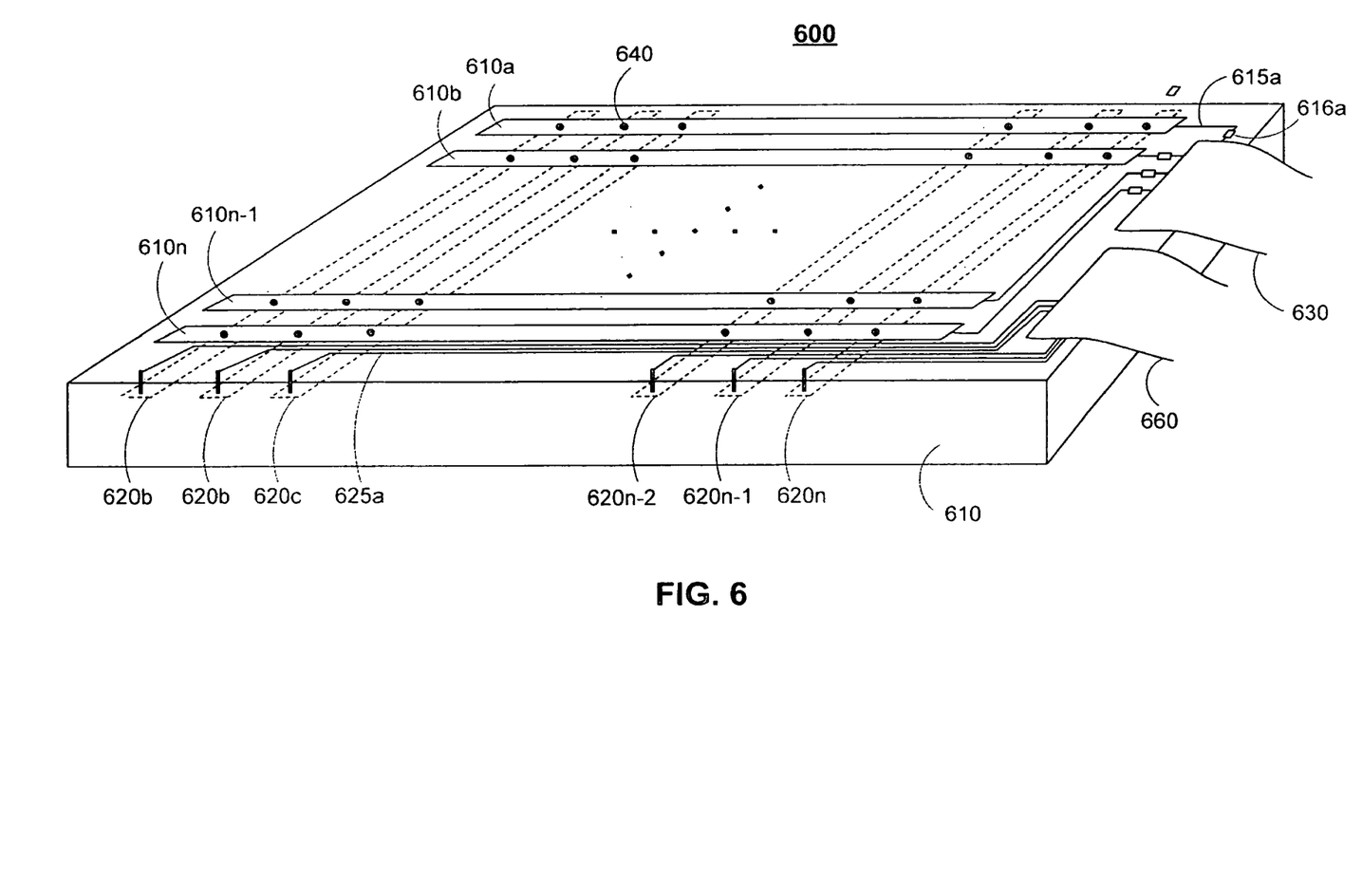
FIG. 6 shows an illustrative touch panel with integrated transparent conductive material resistors in which the flex circuits are bonded to the same edge, on the same side of the panel in accordance with an embodiment of the present invention.

Metal traces 415 and 425 can be beneficial for this arrangement because they allow the use of compact flex circuits 430 and 460. Flex circuits 430 and 460 only occupy a small portion of the edges of touch panel. These flex circuits can be significantly smaller than the size of flex circuits that would be required to directly couple to row traces 420 and column traces 410. For example, coupling flex circuitry directly to the row and column traces may require the flex circuits to span nearly the entire edge of the touch panel. FIGS. 5 and 6 show two other exemplary arrangements that can be made by using metal traces to couple electrode rows and electrode columns to their respective flex circuits.

FIG. 5 shows an illustrative touch panel 500 in which the flex circuits are bonded to the same edge, on directly opposite sides of dielectric 501. This arrangement can be made by running metal traces 525 along the edge of dielectric 501. Connecting the flex circuits in this arrangement can minimize the area of touch panel 500 needed for connectivity and can reduce the overall size of touch panel 500. Further, a single flex circuit can be fabricated to connect to rows 520 and columns 510 on directly opposing sides of the same edge of the substrate. Connecting the flex circuits in this arrangement can minimize the area of touch panel 500 needed for connectivity and can reduce the overall size of touch panel 500.

FIG. 6 shows an illustrative touch panel 600 in which the flex circuits are bonded to the same edge, on the same side of dielectric 601. This arrangement can be made by running metal traces through dielectric 601 in order to connect rows 620 to the top surface of dielectric 601 and then running metal traces 625 along the edge of the top surface of dielectric 601. Connecting the flex circuits in this arrangement can minimize the area of touch panel 600 needed for connectivity and can reduce the overall size of touch panel 600. Further, a single flex circuit can be fabricated to connect to rows 620 and columns 610.

Many other arrangements of flex circuits on the touch panels are possible through the use of metal traces in this manner. In some embodiments, both electrode rows and electrode columns can be coupled to their respective flex circuits using metal traces. In some other embodiments, only one set of electrodes are couples to their flex circuit using metal traces. For example, in the embodiment of FIG. 5 rows 520 can be coupled to a flex circuit using metal traces, while columns 510 can be coupled directly to their flex circuit.

While the use of metal traces has many advantages, routing signals along metal traces 415 and 425 has one drawback. Metal traces 415 and 425 can act like antennas and may cause radio-frequency interference (RFI) signals to be coupled to the sensing circuits. These RFI signals may adversely affect the operation of the touch screen and the accuracy at which touch screen 400 is able to detect user input. As the size of touch screen 400 increases, the lengths of metal traces 415 and 425 also increase, thereby increasing the affect of the RFI signals.

In accordance with this invention, the metal traces can be broken and resistors 416 and 426 can be inserted into the signal paths in order to reduce the affect of the RFI signals. Resistors 416 and 426 can preferably be fabricated using the same transparent conductive material used to form traces 410 and 420. For example, resistors 416 and 426 may be formed from ITO.

Figure 7:
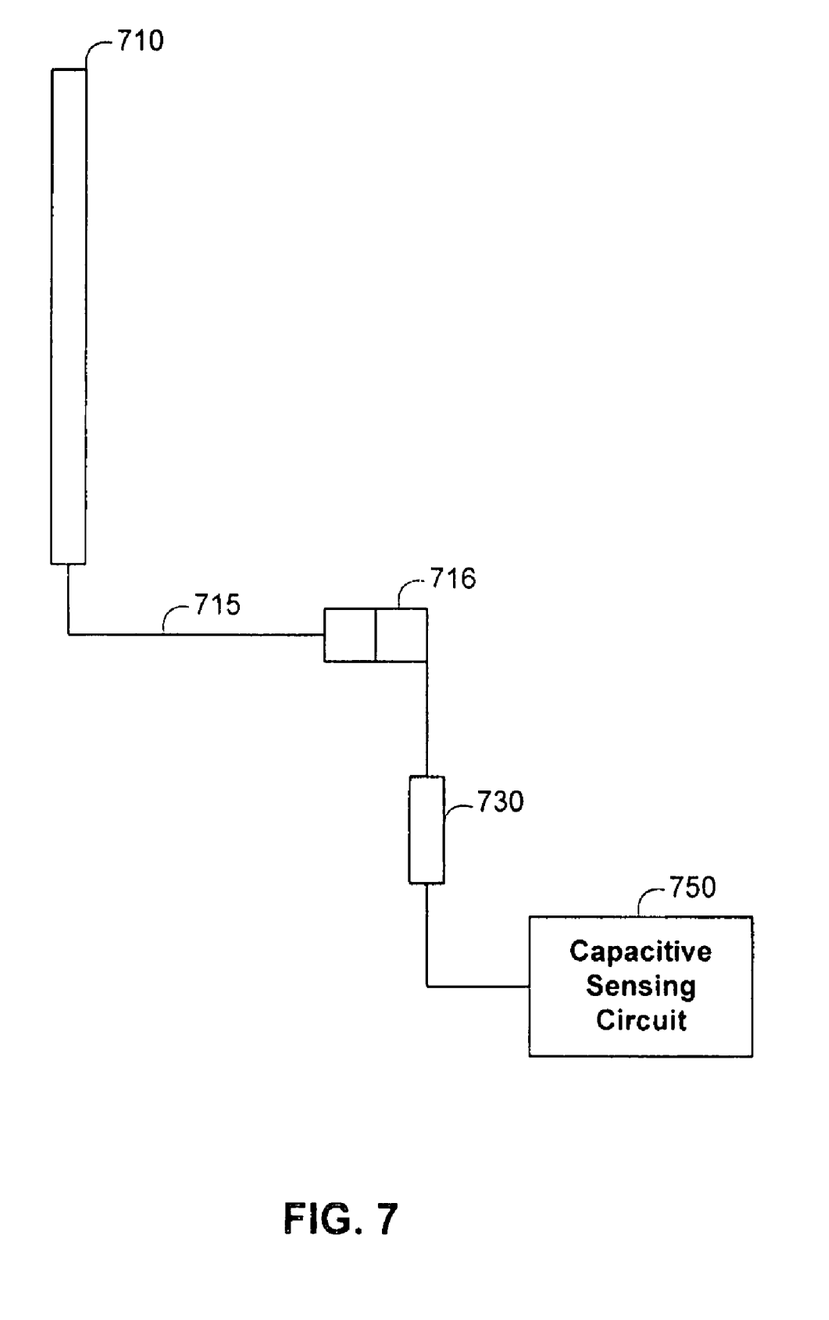
FIG. 7 shows a single illustrative indium tin oxide (ITO) electrode column that is connected to a capacitive sensing circuit via a metal trace, an ITO resistor and a flex circuit in accordance with an embodiment of the present invention.

FIG. 7 shows a single illustrative ITO column trace 710 that is connected to a capacitive sensing circuit 750 via a metal trace 726, an ITO resistor 726 and a flex circuit 730. The ITO may have a sheet resistivity of approximately 200 Ohms per square unit, making the resistance of resistor 746 approximately equal to 400 Ohms. It should be understood that any other suitable transparent conductive material may be used to form column trace 710 and resistor 726.

Figure 8:
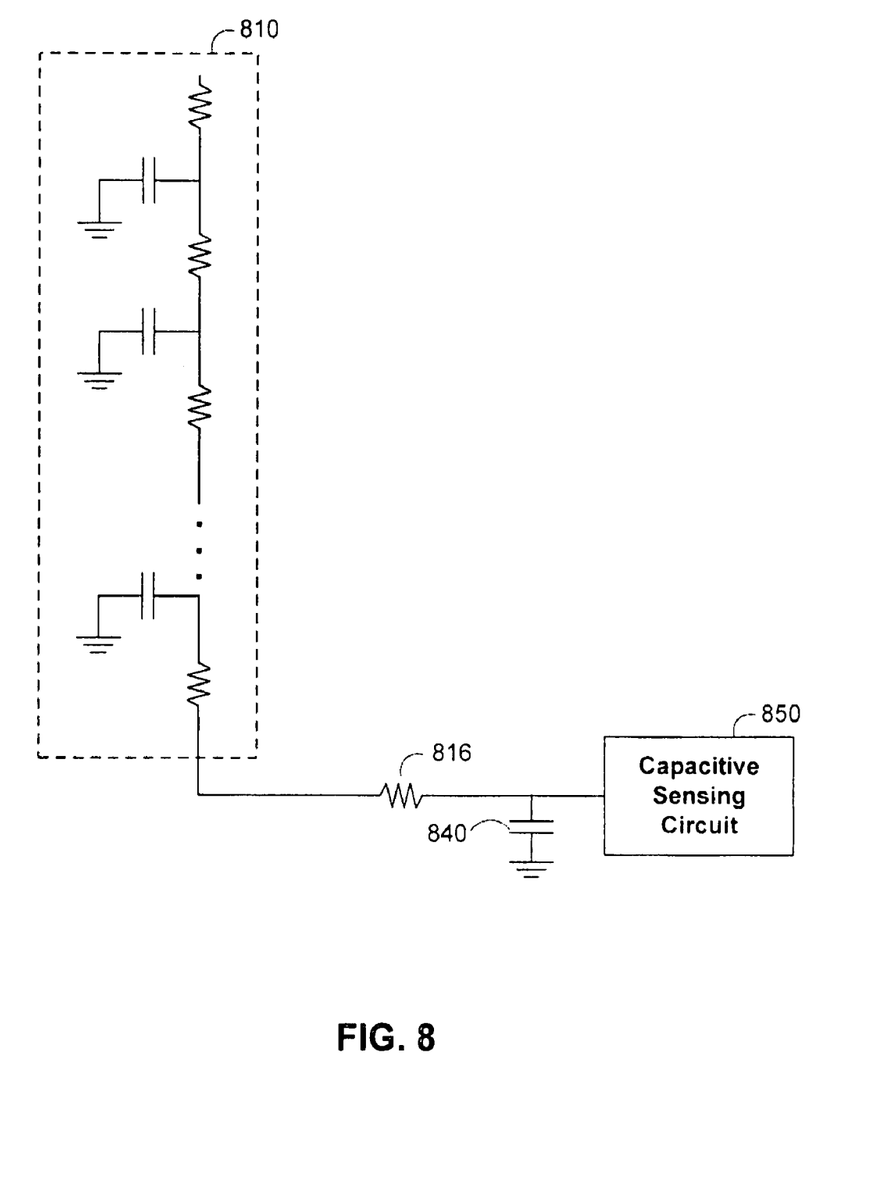
FIG. 8 shows a schematic illustration of the elements of FIG. 7 in accordance with an embodiment of the present invention.

FIG. 8 shows a schematic illustration of the elements of FIG. 7. Sensing line 820 can be modeled as a continuously distributed capacitance. The resistivity of metal trace 825 and flex circuit 830 can be ignored as being negligible. Finally, ITO resistor 826 in conjunction with capacitor 840 forms a low-pass filter. Capacitor 840 represents the input capacitance of capacitive sensing circuit 850 as well as the capacitance of the flex circuitry that is used to couple metal trace 825 to capacitive sensing circuit 850. In this embodiment the capacitance of capacitor 840 can be approximated as 40 pf. With the proper resistance values, this low-pass filter can preferably block or at least significantly attenuate the RFI signals picked up by the metal traces before they are detected at the capacitive sensing circuit. For example, a low-pass filter with a capacitance value of 40 pf and a resistance value of 400 Ohms has a calculated cut-off frequency of 10 MHz. In other words, the resistance and capacitance combination formed by inserting ITO resistors into the metal traces of a touch panel can block most signals with a frequency higher than 1 GHz. This cut-off frequency is suitable to block most of the RFI from entering the capacitive sensing circuitry. The size of ITO resistor 826 can be adjusted to obtain an appropriate resistance value in order to ensure an appropriate cut-off frequency value.

Inserting the transparent conductive material resistors within the metal traces in this manner can be accomplished with little or no incremental cost because the transparent conductive material may already be patterned on the surface of the touch panel to create the transparent conductive material electrode rows and columns. These electrode rows and columns are generally formed by depositing an transparent conductive material layer over the substrate surface, and then by etching away portions of the transparent conductive material layer in order to form the lines. Therefore the transparent conductive material resistors, in accordance with the invention, may be formed as part of the process of creating the electrode rows and columns. Then, instead of etching away all of the extra portions of the transparent conductive material layer, some of the portions transparent conductive material may be kept to serve as transparent conductive material resistors. In some other embodiments, multiple layers of transparent conductive material may be deposited over the substrate surface thereby allowing the transparent conductive material resistors to be formed separately from the electrode rows and columns. In some embodiments, the transparent conductive material used to form the resistors can be different than the transparent conductive material resistors used to form the electrode rows and columns.

Furthermore, there is an additional benefit to leaving additional transparent conductive material on the surface of a touch panel. As should be appreciated, the areas with transparent conductive material tend to have lower transparency than the areas without transparent conductive material. This is generally less desirable for the user as the user can distinguish the lines from the spaces therebetween, i.e., the patterned transparent conductive material can become quite visible thereby producing a touch screen with undesirable optical properties. In order to prevent the aforementioned problem, rather than simply etching away all of the transparent conductive material, the dead areas (the uncovered spaces) may be subdivided into unconnected electrically floating transparent conductive material pads, i.e., the dead areas may be patterned with spatially separated pads. The pads are typically separated with a minimum trace width. Furthermore, the pads are typically made small to reduce their impact on the capacitive measurements. This technique attempts to minimize the appearance of the transparent conductive material by creating a uniform optical retarder. That is, by seeking to create a uniform sheet of transparent conductive material, it is believed that the panel will function closer to a uniform optical retarder and therefore non-uniformities in the visual appearance will be minimized. Thus, in some embodiments, in addition to floating transparent conductive material pads, transparent conductive material resistor blocks can be patterned on the surface of the touch panel to provide RFI blocking as well as increasing the uniformity of the visual appearance of the touch panel.

Figure 9:
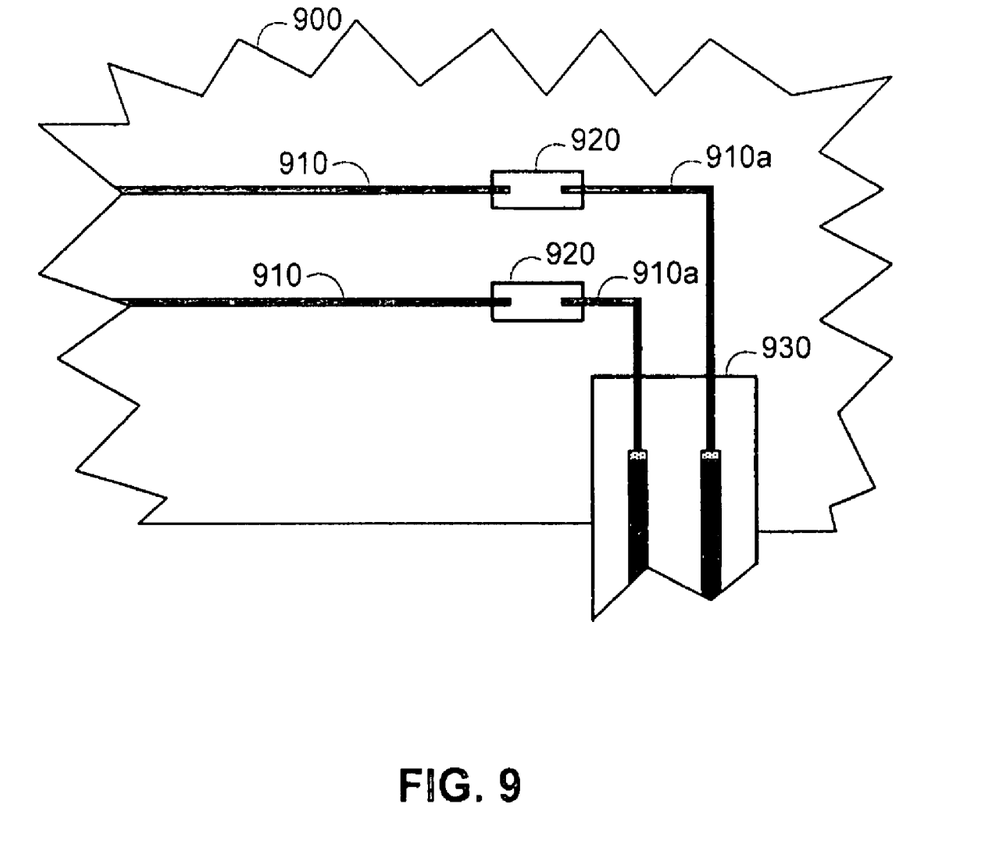
FIGS. 9 and 10 show two exemplary configurations for connecting a flex circuits to metal traces having integrated transparent conductive material resistors in accordance with an embodiment of the present invention.
Figure 10:
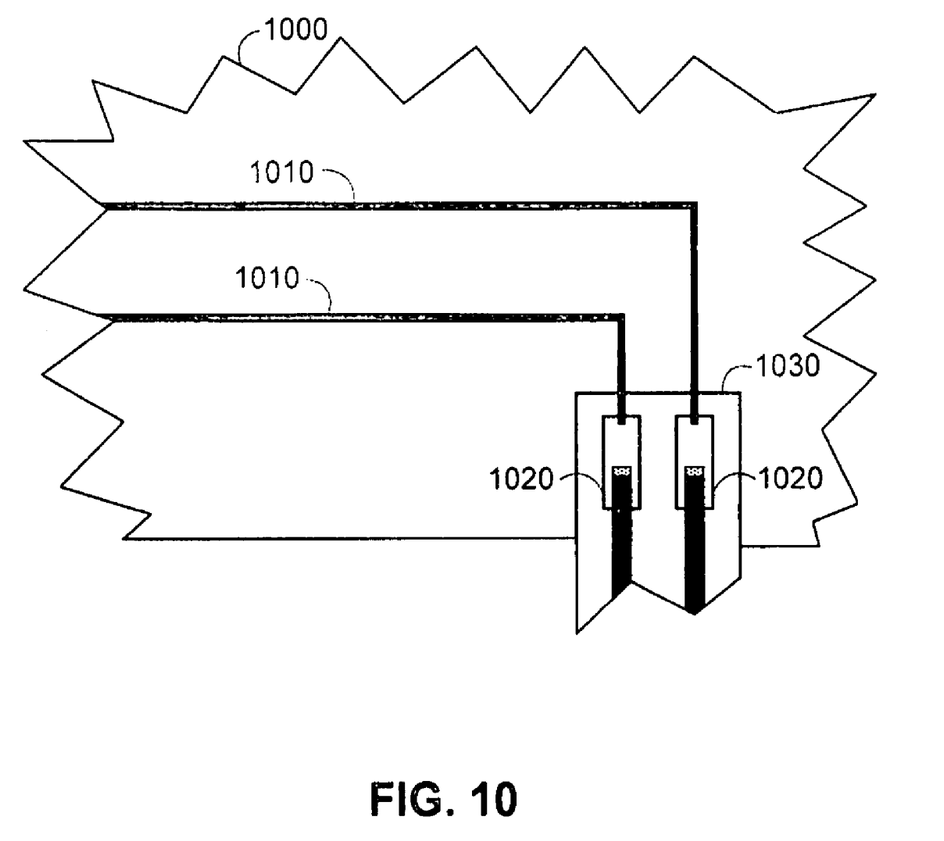

FIGS. 9 and 10 show two exemplary configurations for connecting a flex circuits to metal traces having integrated transparent conductive material resistors. In FIG. 9, metal traces 910 are etched into the top surface of touch panel 900. Near the edge of touch panel 900, metal traces 910 are broken and transparent conductive material resistors 920 are inserted. After transparent conductive material resistors 920 metal traces portions 910a continue and are connected to the copper traces of flex circuit 930. While metal trace portions 910a do not benefit from the RFI blocking of transparent conductive material resistors 920, these portions can be made sufficiently short to minimize the affect of the RFI.

FIG. 10 shows another configuration for connecting flex circuits to metal traces having integrated transparent conductive material resistors. Metal traces 1010 are etched into the top surface of touch panel 1000 and near the edge of touch panel 1000, metal traces 1010 are broken and transparent conductive material resistors 1020 are inserted. Transparent conductive material resistors 1020 are formed sufficiently close to the edge of touch panel 1000 so that flex circuit 1030 can be bonded directly to transparent conductive material resistors 1020. Thus, in this configuration, transparent conductive material resistors 1020 are able to block the RFI for the entirety of metal traces 1010.

Figure 11:
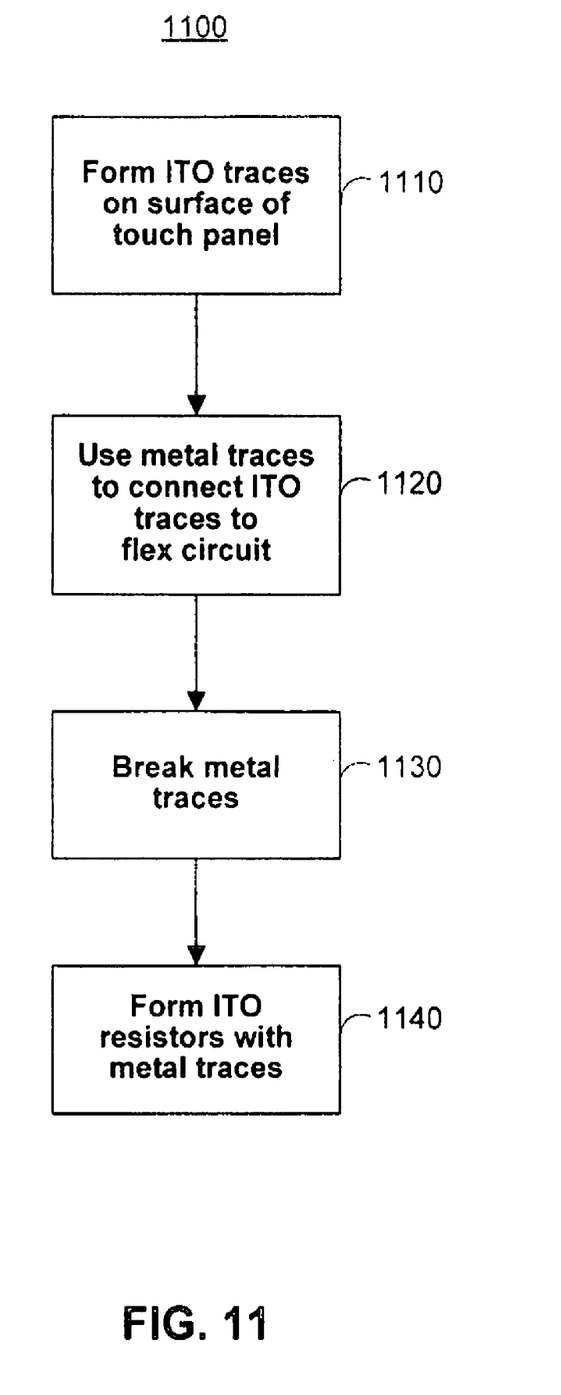
FIG. 11 shows a flowchart of an illustrative process for fabricating a touch panel with integrated transparent conductive material resistors in accordance with an embodiment of the present invention.

FIG. 11 shows a flowchart of process 1100 for fabricating a touch panel with integrated transparent conductive material resistors in accordance with the present invention. At step 1110 transparent conductive material traces are formed on a surface of a touch panel. At step 1120 metal traces are formed to connect the transparent conductive material traces to a flex circuit connector. At step 1130 the metal traces are broken and at step 1140 transparent conductive material resistors are formed within the breaks of the metal traces. While this invention has been primarily described with reference to breaking metal traces to form the transparent conductive material resistors, it should be understood these steps may also be accomplished using any number of suitable techniques. For example, rather than breaking a metal trace, a metal trace may be formed having a gap that is sized to accommodate an transparent conductive material resistor. Furthermore, in some embodiments, the transparent conductive material layer may be fabricated before the metal trace layer. In these embodiments, the metal trace portions may actually be formed around the transparent conductive material resistors.

Thus it is seen that the systems and method for fabricating touch panels with integrated transparent conductive material resistors in accordance with the present invention are provided. Those skilled in the art will appreciate that the invention can be practiced by other than the described embodiments, which are presented for purposes of illustration rather than of limitation, and the invention is limited only by the claims which follow.

What is claimed is:

1. A touch panel having integrated transparent conductive material resistors, comprising:
   a pattern of transparent conductive material traces formed from a deposition of a transparent conductive material on a first surface of the touch panel, the pattern of transparent conductive material traces deposited in a display area of the touch panel and the same deposition of the transparent conductive material also forming a plurality of transparent conductive material resistors in a non-display area of the touch panel; and
   a plurality of metal traces connected to the pattern set of transparent conductive material traces;
   wherein the plurality of transparent conductive material resistors are connected to the metal traces and configured to form a portion of a low pass filter for blocking electromagnetic interference on the connected metal traces.

2. The touch panel of claim 1, wherein the transparent conductive material resistors are connected between the metal traces and capacitive sensing circuitry.

3. The touch panel of claim 1, wherein the transparent conductive material resistors have a resistance of approximately 400 Ohms.

4. The touch panel of claim 1, the low-pass filters having a cut-off frequency of approximately 10 MHz.

5. The touch panel of claim 4, wherein the low-pass filters block signals having frequencies greater than approximately 1 GHz.

6. The touch panel of claim 2, wherein the transparent conductive material resistors increase the sensitivity of the capacitive sensing circuitry.

7. The touch panel of claim 1, further comprising flex circuitry connected directly to the transparent conductive material resistors.

8. The touch panel of claim 1, further comprising connecting the transparent conductive material resistors adjacent to an end of the metal traces.

9. The touch panel of claim 1, the deposition of transparent conductive material having portions removed to form the transparent conductive material traces and resistors.

10. The touch panel of claim 1, wherein the transparent conductive material comprises at least one of indium tin oxide (ITO), conductive clear polymer, and antimony tin oxide (ATO).

11. A computer system having a touch panel with integrated transparent conductive material resistors, comprising:
   a processor configured to execute instructions and to carry out operations associated with the computer system;

a display device that is operatively coupled to the processor;

a touch panel that is operatively coupled to the processor, the touch panel being a substantially transparent panel that is positioned in front of the display, the touch panel including
- a pattern of transparent conductive material traces formed from a deposition of a transparent conductive material on a first surface of the touch panel, the pattern of transparent conductive material traces deposited in a display area of the touch panel and the same deposition of the transparent conductive material also forming a plurality of transparent conductive material resistors in a non-display area of the touch panel; and
- a plurality of metal traces connected to the pattern set of transparent conductive material traces;
- wherein the plurality of transparent conductive material resistors are connected to the metal traces and configured to form a portion of a low pass filter for blocking electromagnetic interference on the connected metal traces.

12. The computer system of claim 11, wherein the transparent conductive material resistors are connected between the metal traces and capacitive sensing circuitry.

13. The computer system of claim 11, wherein the transparent conductive material resistors have a resistance of approximately 400 Ohms.

14. The computer system of claim 11, the low-pass filters having a cut-off frequency of approximately 10 MHz.

15. The computer system of claim 14, wherein the low-pass filters block signals having frequencies greater than approximately 1 GHz.

16. The computer system of claim 12, wherein the transparent conductive material resistors increase the sensitivity of the capacitive sensing circuitry.

17. The computer system of claim 11, further comprising flex circuitry connected directly to the transparent conductive material resistors.

18. The computer system of claim 11, further comprising connecting the transparent conductive material resistors adjacent to an end of the metal traces.

19. The computer system of claim 11, the deposition of transparent conductive material having portions removed to form the transparent conductive material traces and the transparent conductive material resistors.

20. The computer system of claim 11, wherein the transparent conductive material comprises at least one of indium tin oxide (ITO), conductive clear polymer, and antimony tin oxide (ATO).

21. A method for fabricating a touch panel having transparent conductive material resistors, comprising:
- forming a plurality of metal traces on the touch panel, the metal traces including one or more breaks; and
- forming a pattern of material traces from a deposition of a-transparent conductive material on a first surface of the touch panel, the pattern of material traces deposited in a display area of the touch panel and the same deposition of the transparent conductive material also forming a plurality of transparent conductive material resistors in a non-display area of the touch panel, the resistors formed within the breaks of the metal traces and configured to form a portion of a low pass filter for blocking electromagnetic interference on the connected metal traces.

22. The method of claim 21, wherein the transparent conductive material comprises at least one of indium tin oxide (ITO), conductive clear polymer, and antimony tin oxide (ATO).

\* \* \* \* \*

UNITED STATES PATENT AND TRADEMARK OFFICE
CERTIFICATE OF CORRECTION

PATENT NO. : 8,400,408 B2  
APPLICATION NO. : 11/818311  
DATED : March 19, 2013  
INVENTOR(S) : Hotelling et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1108 days.

Signed and Sealed this  
Ninth Day of December, 2014

Michelle K. Lee  
*Deputy Director of the United States Patent and Trademark Office*